United States Patent [19]

Bresciani

[11] Patent Number: 5,342,911
[45] Date of Patent: Aug. 30, 1994

[54] CROSSLINKED POLYACRYLIC ACIDS HAVING LOW SOLVENT RESIDUE, A PROCESS FOR THE PREPARATION THEREOF AND THE USE THEREOF AS THICKENING AGENTS

[75] Inventor: Angelo Bresciani, Bergamo, Italy
[73] Assignee: 3V Inc., Weehawkin, N.J.
[21] Appl. No.: 111,742
[22] Filed: Aug. 25, 1993
[51] Int. Cl.$^5$ ................................................ C08F 2/00
[52] U.S. Cl. .................................... 526/216; 524/729; 526/230.5; 526/317.1; 526/318.5; 526/334
[58] Field of Search .................. 526/216, 230.5, 317.1, 526/318.5, 334; 524/729

[56] References Cited

U.S. PATENT DOCUMENTS 4,267,103  5/1981  Cohen ............................ 526/216 X
4,996,274  2/1991  Hsu ................................ 526/216 X

*Primary Examiner*—Judy M. Reddick
*Attorney, Agent, or Firm*—Griffin, Butler, Whisenhunt & Kurtossy

[57] ABSTRACT

A crosslinked acrylic acid polymer or crosslinked acrylic acid copolymer consisting of at least 80% of acrylic acid and containing less than 5 ppm of methylene chloride obtained by a process comprising the radicalic polymerization of monomers in a solvent mixture consisting of a mixture of methylene chloride and a carboxylic ester having formula $$R-COO-R_1$$

wherein R is hydrogen, methyl or ethyl group, $R_1$ is $C_1$–$C_3$ alkyl group, wherein said solvent mixture consists of 60–75% v/v of methylene chloride and 40–25% v/v of carboxylic ester, or, alternatively, dimethyl or diethylcarbonate is used instead of the carboxylic ester, together with a cross-linking agent, in an amount from 0.3 and 4% w/w, calculated on the monomer, and an appropriate free radical initiator as catalyst at a temperature ranging from 35° C. and reflux temperature. The polymers and copolymers are useful as thickening agents for cosmetic and pharmaceutical formulations.

6 Claims, No Drawings

CROSSLINKED POLYACRYLIC ACIDS HAVING LOW SOLVENT RESIDUE, A PROCESS FOR THE PREPARATION THEREOF AND THE USE THEREOF AS THICKENING AGENTS

The present invention relates to crosslinked polyacrylic acids having low solvent residue, a process for the preparation thereof and to the use thereof as thickening agents.

Polymers or copolymers of unsaturated carboxylic acids, crosslinked with olefinic polyfunctional compounds have been well known for a long time.

The most typical monomers include acrylic, methacrylic, maleic, itaconic acids and their anhydrides.

Homopolymer of acrylic acid or its copolymers containing up to 20% of other monomers are particularly known. These last ones can be esters #such as alkyl acrylates, alkyl maleates, alkyl itaconates, or nitriles, such as acrylonitrile or amides such as acrylamide, maleimide.

As crosslinking agent whatever polyfunctional monomer containing at least two end-chain vinylidenic groups can be used. Esters of acrylic or methacrylic acid with polyols, such as hexane diacrylate, trimethylolpropane triacrylate, pentaerythritol triacrylate or amides, such as methylene bisacrylamide or preferably polyalchenylpolyethers, such as butanediol diallylether, trimethylolpropane triallylether, pentaerythritol tetraallylether or saccharose polyallylethers.

These polymers have been widely used as thickeners in different industrial fields.

If used in small amounts and particularly as salts with monovalent alkaline metals or amines, they can thicken water and organic solvents as well.

There is wide literature concerning both the preparation procedures of these polymers and their uses. They are mainly prepared by polymerization of monomers, with crosslinking agents in solvents in which monomers can be well soluble and polymers insoluble.

As solvents, aliphatic or aromatic hydrocarbons, ketones, esters, ethers, chlorinated hydrocarbons, and their mixtures, preferably with low boiling points can be used.

The solvents used for the polymerization have a great influence on the features and quality of the obtained polymers.

Generally, a polymer is considered good if it has the following features:
 a) high thickening capacity even at very low concentrations;
 b) soft and smooth appearance of the thickened formulates;
 c) very high trasparency of the aqueous gels;
 d) very low content of foreign matters, such as residues of monomers or solvents;
 e) it must be practically colourless and odourless.

These features depend only or mainly on the solvent used for the polymerization.

The solvents that gave the best results till today, i.e. polymers having the optimal features previously described, are benzene and methylene chloride; this last one is to be preferred also for toxicological reasons, as the thickened products obtained using polymers prepared with this solvent have-a smoother appearance than those prepared with benzene. Using other solvents interesting from the toxicological point of view, as they are safer or practically harmless, such as methyl alcohol, ethyl or propyl alcohol or formic and acetic acid, give poor quality polymers, which are practically useless either for their low viscosity, or for the graining and hazy appearance of the obtained gels.

These synthetic thickeners anyhow prepared contain residues of solvents in small amounts which can range within wide limits, according to the solvent and the purification procedure used and also on the particular use to which they are intended.

Generally, the residual benzene or methylene chloride varies between 500 and 1000 ppm. Commercial products containing 100 ppm or less of solvent residue are unusual. In spite of the low boiling points, the question of the removal of these residual solvents from the polymers has not been solved yet.

The use of these polymers as thickening agents is mainly widespread in textile print and in cosmetic and pharmaceutical formulations. In cosmetic and pharmaceutical field, the polymer quality is very important, namely their viscosity capacity, since this relates to the possibility to prepare formulates of smooth appearance or gels and shampoos of the greatest trasparency. The impurity content is particularly important and among them, mainly the residual solvent content.

In cosmetic and pharmaceutical formulations the ingredient impurity and toxicity are carefully evaluated and they are used only in products complying with strict requirements. Therefore, concerning the polymer use, the determining factor is the achievement of very low, practically negligible levels, of residual solvents, if the solvents have a certain degree of toxicity.

In these cases, the presence of a solvent, such as benzene, which is highly toxic and dangerous, even if present in negligible traces, makes the polymer use very problematic or even prohibitive.

Even though the toxicity of methylene chloride is not of a particular concern and not comparable to benzene, too high residual amount of this solvent is not well accepted either for the toxicological risk or for the possibility of allergic reactions.

For these reasons, different devices or drying-processes have been tried in order to reach the low levels of residual solvent required by the cosmetic and pharmaceutical industry for the polymers. Until today the results are disappointing: a satisfactory solution from a technological and economic point of view has not yet been found. The various attempts of special drying methods have been negative or processes, such as the one described in the U.S. Pat. No. 5093472, require long times and they are so laborious, complex and expensive to be technologically and economically prohibitive.

DOS 2 927 132 claims a process for the polymerization of acrylic monomers in solvents mixtures with 1–20% of esters containing from 3 to 6 atoms of carbon, 80–99% v/v of cyclohexane or aliphatic chlorinated hydrocarbons, among which methylene chloride is also included, although that solvent is never quoted expressly either in the general description or in the numerous descriptive examples. However, working with solvents mixture in ratios according to Patent DOS 2 927 132, polymers of good quality, but with methylene chloride contents higher than those of the polymers according to the present invention, are obtained.

U.S. Pat. No. 4996274 claims polymers obtained in a mixed reaction medium of ethyl acetate and normal or cyclohexane. Such polymers are claimed to have a good transmittance, but the appearance looks quite graining.

The need of a process valid from a technological and economic point of view in order to obtain polymers with negligible methylene chloride content is therefore still topical.

Surprisingly, it has been found that using for the polymerization a solvent mixture in well-defined ratios of methylene chloride with a carboxylic ester having the following formula:

$$R-COO-R_1$$

were R is hydrogen, methyl or ethyl group and $R_1$ is $C_1$-$C_3$ alkyl group, polymers with the same optimal features of the ones obtained using only methylene chloride, but with residual methylene chloride lower than 5 ppm can be obtained without special or expensive drying methods, as a post-drying with fluid beds dryers, but simply by evaporating the solvents mixtures.

It has also been found that good results are achieved if in the solvent mixture, and in the same ratios, dimethyl- or diethylcarbonate is used instead of the carboxylic ester.

Accordingly, it is an object of the present invention to provide crosslinked acrylic acid polymers or crosslinked acrylic acid copolymers consisting of at least 80% of acrylic acid and containing less than 5 ppm of methylene chloride obtained by a process comprising the radicalic polymerisation of monomers in a solvent mixture consisting of methylene chloride and a carboxylic ester having formula $$R-COO-R_1$$

wherein R is hydrogen, methyl or ethyl group, $R_1$ is $C_1$-$C_3$ alkyl group, wherein said solvent mixture consists of 60–75% v/v of methylene chloride and 40–25% v/v of carboxylic ester together with a crosslinking agent, in the amount from 0,3 and 4% w/w, calculated on the monomer, and an appropriate free radical initiator as catalyst at a temperature ranging from 35° C. to reflux temperature.

In another embodiment, it is a further object of the present invention, to provide the polymer obtained by a process as above described, characterized in that dimethyl- or diethylcarbonate is used instead of the carboxylic ester.

In case of mixture of solvents containing amounts of methylene chloride lower than 60%, polymers of poor quality are obtained, i.e. polymers with low viscosity which do not give smooth formulates, even with low content of methylene chloride.

If the methylene chloride is higher than 75%, polymers with optimal features but with methylene chloride content much higher than 5 ppm are obtained.

The polymerization is carried out according to conventional methods as described in the cited literature and in any case well known to the skilled technician.

The monomer or comonomer polymerization occurs in the presence of an appropriate catalyst in inert atmosphere (for example nitrogen or argon).

The polymerization temperature ranges from 35° C. to the solvent mixture reflux temperature. Free radical initiators can be used as catalysts, such as for example (2-ethylhexyl )peroxydicarbonate, di(sec-butyl)peroxodicarbonate, di(cyclohexyl)peroxydicarbonate, di(-cetyl)peroxodicarbonate, di(n-propyl) peroxydicarbonate, lauroyl peroxide and other peroxides and peroxydicarbonates. The slurry polymer is dried by distillating off the solvent mixture and is further warm-dried under vacuum. The so obtained polymers in the form of a powder have a solvent residue lower than 5 ppm and can be used as thickening agents in cosmetic and pharmaceutical formulations.

The following Examples further illustrate the invention. Comparative Examples 1–5 describe the preparation of polymers with reaction media according to the prior art, particularly, in Comparative Example 1, only methylene chloride is used. In Comparative Examples 2–3, the ethyl acetate/methylene chloride mixture according to the ratios disclosed in DOS 2 927 132 is used, and in Comparative Examples 4–5 the mixture described in U.S. Pat. No. 4,996,274 is used. Examples 1–5 refer to the present invention.

COMPARATIVE EXAMPLE 1

1200 ml of methylene chloride were put into a flask, 158 g of acrylic acid and 1.36 g of pentaerythritol triallylether were added. Nitrogen was blown for 20 minutes, then 1.6 g of di(cetyl)peroxydicarbonate were added.

The flask was slowly heated in nitrogen atmosphere until slow reflux was obtained and stirred for 10 hours. The obtained slurry polymer was dried removing the solvent by distillation in a rotating evaporator at atmospheric pressure and warming at a temperature of 80° C.

When the distillation was completed vacuum was applied until 30–40 residual torr going on with the polymer drying, by warming at 80° C. for 8 hours. 180 g of polymer as a white powder were obtained.

COMPARATIVE EXAMPLE 2

A polymer was prepared according to the same procedure of Comparative Example 1, but using a 80/20 (v/v) methylene chloride/ethyl acetate mixture instead of methylene chloride only.

COMPARATIVE EXAMPLE 3

A polymer was prepared according to the same procedure of Comparative Example 1, but using a 90/10 (v/v) methylene chloride/ethyl acetate mixture.

COMPARATIVE EXAMPLE 4

A polymer according to Example 4 of U.S. Pat. No. 4,996,274 was prepared, carrying out the reaction in a 50/50 (v/v) cyclohexane/ethyl acetate mixture at the temperature of 55 ° C.

COMPARATIVE EXAMPLE 5

A polymer according to Example 4 of U.S. Pat. No. 4,996,276 was prepared, carrying out the reaction in a 50/50 (v/v) cyclohexane/ethyl acetate mixture at the temperature of 60° C.

EXAMPLE 1

A polymer was prepared according to the same procedure of Comparative Example 1, but using a 70/30 (v/v) methylene chloride/ethyl acetate mixture, according to the present invention.

EXAMPLE 2

A polymer was prepared according to the same procedure of Comparative Example 1, but using a 75/25 (v/v) methylene chloride/ethyl formate mixture, according to the present invention.

EXAMPLE 3

A polymer was prepared according to the same procedure of Comparative Example 1, but using a 60/40 (v/v) methylene chloride/ethyl acetate mixture, according to the present invention.

EXAMPLE 4

A polymer was prepared according to the same procedure of Comparative Example 1, but using a 55/45 (v/v) methylene chloride/ethyl formate mixture.

EXAMPLE 5

A polymer was prepared according to the same procedure of Comparative Example 1, but using a 70/30 (v/v) methylene chloride/dimethylcarbonate, according to the present invention.

EXAMPLE 6

The polymers obtained in the Comparative Examples 1-5 and in the Examples 1-5 were analyzed for the determination of methylene chloride residue by means of head space gaschromatography.

The polymers were also used to prepare aqueous gels according to the following method:

2.5 g of polymer were dispersed into 500 ml of demineralized water, and strongly stirred for 1-2 hours. The pH was adjusted to $7\pm0.2$ by adding 10% NaOH and the dispersion stirred for 1-2 hours more.

The viscosity was measured at 25° C. with a Brookfield viscosimeter, spindle n. 7 at 20 rpm.

The transmittance was determined by means of a spectrophotometer at 425 nm and with 1 cm cell.

The appearance of the obtained gel was judged visually.

The results are shown in the following Table 1.

TABLE 1

COMPARISON BETWEEN THE POLYMERS OBTAINED ACCORDING TO THE PRIOR ART AND TO THE PRESENT INVENTION

| Example | Ester | CH$_2$Cl$_2$/Ester ratio (vol/vol) | CH$_2$Cl$_2$ residue (ppm) | Viscosity at 0,5% | 0.5% aqueous gel transmittance (%) | Aspect |
|---|---|---|---|---|---|---|
| Compar. 1 | — | — | 415 | 53.000 | 94,5 | smooth |
| Compar. 2 | Ethyl acetate | 80/20 | 47 | 51.000 | 95 | smooth |
| Compar. 3 | Ethyl acetate | 90/10 | 107 | 49.000 | 94 | smooth |
| Compar. 4 | Ethyl acetate cyclohexane 50/50 | | — | 52.000 | 94 | graining |
| Compar. 5 | Ethyl acetate cyclohexane 50/50 | | — | 48.000 | 93 | graining |
| 1 | Ethyl acetate | 70/30 | 2 | 51.000 | 95 | smooth |
| 2 | Ethyl acetate | 75/25 | 3 | 49.000 | 96 | smooth |
| 3 | Ethyl acetate | 60/40 | 1.5 | 50.000 | 94,5 | almost smooth |
| 4 | Ethyl formate | 55/45 | 2 | 47.000 | 87 | graining |
| 5 | Dimethylcarbonate | 70/30 | 3 | 50.000 | 96 | smooth |

I claim:

1. A crosslinked acrylic acid polymer consisting of at least 80% of acrylic acid and containing less than 5 ppm of methylene chloride obtained by a process comprising the radicalic polymerization of monomers in a solvent mixture consisting of a mixture of methylene chloride and at least one cosolvent selected from the group consisting of:

(A) a carboxylic ester having formula $$R-COO-R_1$$

wherein R is hydrogen, methyl or ethyl group, $R_1$ is $C_1-C_3$ alkyl group, and (B) dimethyl or diethylcarbonate, and wherein said solvent mixture consists of 60-75% v/v of methylene chloride and 40-25% v/v of the cosolvent, said solvent mixture comprising, a crosslinking agent in an amount from 0.3 to 4% w/w, calculated on the monomer, and a free radical initiator as catalyst, said polymerization being carried out at a temperature ranging from 35° C. and reflux temperature.

2. A polymer obtained by a process according to claim 1, wherein said mixture consists of methylene chloride/ethyl acetate in the respective ratio of 70/30 (v/v).

3. A polymer obtained by a process according to claim 1, wherein said mixture consists of methylene chloride/ethyl acetate in the respective ratio of 60/40 (v/v).

4. A polymer obtained by a process according to claim 1, wherein said mixture consists of methylene chloride/ethyl formate in the respective ratio of 75/25 (v/v).

5. A polymer obtained by a process according to claim 1, wherein said mixture consists of methylene chloride/dimethylcarbonate in the respective ratio of 70/30 (v/v).

6. A polymer obtained by a process according to claim 1, where in pentaerythritol triallyl ether is the crosslinking agent and di(cetyl)peroxydicarbonate is the catalyst.

* * * * *